United States Patent [19]

Ward, Jr.

[11] Patent Number: 4,846,983
[45] Date of Patent: Jul. 11, 1989

[54] NOVEL CARBAMATE ADDITIVES FOR FUNCTIONAL FLUIDS

[75] Inventor: William C. Ward, Jr., Painesville, Ohio

[73] Assignee: The Lubrizol Corp., Wickliffe, Ohio

[21] Appl. No.: 832,569

[22] Filed: Feb. 21, 1986

[51] Int. Cl.⁴ ............... C10M 135/18; C10M 135/16; C10L 1/24
[52] U.S. Cl. .................... 252/33.6; 252/45; 252/46.4; 252/51.5 R; 44/68
[58] Field of Search ............ 252/46.4, 45, 51.5 R, 252/33.6; 44/68; 556/38

[56] References Cited

U.S. PATENT DOCUMENTS

| | | | |
|---|---|---|---|
| 3,419,589 | 12/1968 | Larson et al. | 260/429 |
| 3,509,051 | 4/1970 | Farmer et al. | 252/33.6 |
| 3,541,014 | 11/1970 | Le Suer | 252/49.7 |
| 4,098,705 | 7/1978 | Sakurai | 252/33.6 |
| 4,164,473 | 8/1979 | Coupland et al. | 252/32.7 |
| 4,259,194 | 3/1981 | de Vries et al. | 252/46.4 |
| 4,259,195 | 3/1981 | King et al. | 252/49.7 |
| 4,265,773 | 5/1981 | de Vries et al. | 252/46.4 |
| 4,266,945 | 5/1981 | Karn | 44/68 |
| 4,272,387 | 6/1981 | King et al. | 252/46.4 |
| 4,283,295 | 8/1981 | de Vries et al. | 252/46.4 |
| 4,285,822 | 8/1981 | de Vries et al. | 252/46.4 |
| 4,289,635 | 9/1981 | Schroeck | 252/32.7 |
| 4,315,826 | 8/1980 | Schlicht et al. | 252/46.4 |
| 4,369,119 | 1/1983 | De Vries et al. | 252/42.7 |
| 4,395,343 | 7/1983 | de Vries et al. | 252/32.7 E |
| 4,402,840 | 9/1983 | de Vries et al. | 252/45 |
| 4,474,673 | 10/1984 | Hunt et al. | 252/42.7 |
| 4,479,883 | 10/1984 | Shaub et al. | 252/32.7 |

OTHER PUBLICATIONS

Lashkhi et al., *Khimiya i Tekhnologiya Topliv i Masel*, No. 12, pp. 33–35, Dec. 1983.

*Primary Examiner*—William R. Dixon, Jr.
*Assistant Examiner*—Jerry D. Johnson
*Attorney, Agent, or Firm*—Forrest L. Collins; Robert A. Franks; Joseph L. Fischer

[57] ABSTRACT

Novel molybdenum or tungsten thiocarbamate additives for functional fluids, e.g., lubricating oils, automatic transmission fluids (ATF), as well as fuel compositions, have been developed. The molybdenum or tungsten carbamate compositions, compounds, complexes and oligomers of the present invention are derived from at least one hydrocarbyl primary amine and impart improved anti-wear properties, anti-oxidant properties, extreme pressure properties and friction modifying properties in functional fluids for internal combustion engines.

56 Claims, No Drawings

1

NOVEL CARBAMATE ADDITIVES FOR FUNCTIONAL FLUIDS

BACKGROUND OF THE INVENTION

1. Field of the Invention

This invention relates generally to novel, metal-containing thiocarbamate additives for functional fluids, e.g., lubricating oils, automatic transmission fluids (ATF's), as well as fuel compositions. This invention more specifically relates to metal compounds, complexes and compositions of thiocarbamates derived from hydrocarbyl primary amines. These metal compounds, complexes, oligomers and compositions are useful as additives which impart improved anti-wear properties, anti-oxidant properties, extreme pressure properties, and friction modifying properties in functional fluids for internal combustion engines.

2. State of the Art

As those skilled in this art are aware, additives impart special properties to functional fluids, particularly lubricants and fuel. They may give these fluids new properties or they may enhance properties already present. One property all lubricants have in common is the reduction of friction between materials in contact. Nonetheless, the art constantly seeks new materials to enhance such friction properties.

Carbamate additives for functional fluids, particularly molybdenum-containing and tungsten-containing carbamate additives for lubricant and fuel compositions have been disclosed in the patent literature and reported in the technical literature.

For example, U.S. Pat. Nos. 4,395,343; 4,402,840; 4,285,822; 4,265,773; 4,272,387; 4,369,119; 4,259,195; 4,259,194; and 4,283,295 all to DeVries and King disclose a variety of molybdenum sulfur and nitrogen containing compounds including dithiocarbamates which are useful as anti-oxidant additives for lubricant compositions. While some of these patents disclose dithiocarbamate metal compounds including molybdenum, all of these compounds, however, are derived from secondary amines according to methods previously described in the art.

U.S. Pat. No. 4,315,826 to Schlicht et al. describes molybdenum dithiocarbamate compounds useful as anti-wear and anti-oxidant additives for lubricating compositions. These compounds are prepared by treating a thiomolybdenum derivative of an alkenylsuccinimide with carbon disulfide.

A molybdenum dihydrocarbyldithiocarbamate compound useful as an additive for lubricants is disclosed in U.S. Pat. No. 4,098,705 to Sakurai et al. This compound is derived from a secondary amine.

In U.S. Pat. No. 3,509,051 to Farmer et al., various molybdenum dialkyldithiocarbamates are disclosed which are derived from secondary amines. These compounds are disclosed as being useful as anti-oxidant and anti-wear additives for lubricating oils.

Metal dithiocarbamates wherein the metal may be molybdenum are disclosed in U.S. Pat. No. 4,479,883 to Shaub et al. as being useful in combination with an ester of a polycarboxylic acid and a glycol or glycerol to provide improved friction reducing properties in lubricating compositions. Complexes of molybdenum oxides and sulfur- and nitrogen-containing moieties which include dialklydithiocarbamates, which have utility as additives for lubricants, are disclosed in U.S. Pat. No. 3,419,589 to Larson et al. and U.S. Pat. No. 4,164,473 to Coupland et al.

U.S. Pat. No. 4,474,673 discloses sulfurized molybdenum-containing friction modifying additives for lubricating oils which are prepared by reacting a sulfurized organic compound having an active hydrogen or potentially active hydrogen with a molybdenum halide.

U.S. Pat. No. 3,541,014 to LeSuer discloses molybdenum complexes of Group II metal-containing compounds, e.g., overbased Group II metal sulfonates, which impart improved extreme pressure properties and anti-wear properties to lubricant compositions.

The review article to Lashkhi et al. in Khimiya i Tekhnologiya Topliv i Masel, Number 12, Pages 33–35, December, 1983, discloses various oil-soluble molybdenum compounds including dithiocarbamates which are useful as friction modifying agents to result in lower fuel consumption in internal combustion engines.

Novel sulfur and phosphorus containing molybdenum compositions which are useful for improving fuel economy for internal combustion engines are disclosed in U.S. Pat. No. 4,289,635 to Schroeck.

U.S. Pat. No. 4,266,945 to Karn discloses molybdenum-containing compositions which are derived from a molybdenum compound, phenol and an amine which compositions are disclosed as being useful as additives in lubricants and fuels.

None of the foregoing disclosures teach nor even suggest a molybdenum carbamate compound, complex or composition which has been derived from a primary amine and which further improves anti-wear properties, anti-oxidant properties, extreme pressure properties and friction modifying properties for functional fluids in general and specifically for lubricant compositions.

SUMMARY OF THE INVENTION

It has been the dramatic discovery of the present invention that molybdenum carbamate compounds may be derived from at least one hydrocarbyl primary amine and which compounds find utility as additives in functional fluids including lubricants as well as fuels.

Further, in accordance with the invention, a novel process for the preparation of the metal carbamate compounds, complexes, oligomers and compositions of the present invention from primary amines has been developed.

Still further, in accordance with the present invention, additives for improving anti-wear properties, anti-oxidant properties, extreme pressure properties and friction modifying properties of lubricant compositions which comprise the compounds, complexes, oligomers and compositions of this invention are provided.

Still further, in accordance with the present invention, concentrates and functional fluids including lubricant compositions, fuel compositions, automatic transmission fluids, hydraulic fluids and metal working fluids which comprise the compounds, complexes, oligomers and compositions of this invention are provided.

These and other aspects and advantages of the invention will be appreciated by those skilled in the art from the detailed description of the invention and the claims which follow

DETAILED DESCRIPTION OF THE INVENTION

The novel compositions of the present invention may be described by the following general formula:

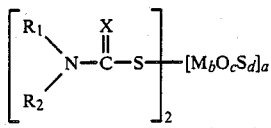  (I)

wherein M is Mo or W, $R_1$ and $R_2$ are independently the same or different and are selected from H and hydrocarbyl with the proviso that at least one of $R_1$ or $R_2$ is H for at least one of the thiocarbamate groups, and at least one of $R_1$ or $R_2$ is hydrocarbyl for each of the thiocarbamate groups where each $R_1$ and $R_2$ of the molecule may vary independently, X is O or S, b is at least 1, and a is at least 1 depending on the oxidation state of M, c is at least 1 depending on the oxidation state of M and d is 0 or at least 1 depending on the oxidation state of M. Generally, a and b will range from 1 to about 5, c will range from 1 to about 6 and d will be 0 or range from 2 to about 10. In a most preferred embodiment, a will be 1 or 2, b will be 1 or 2, c will be 1 or 2 and d will be 0 or 2.

As used herein and throughout this specification, the term "hydrocarbon-based substituent" or "hydrocarbyl" denotes a substituent having carbon atoms directly attached to the remainder of the molecule and is predominantly hydrocarbyl in character within the context of this invention. Such substituents include the following:

1. Hydrocarbon substituents, that is, aliphatic (for example alkyl or alkenyl), alicyclic (for example cycloalkyl or cycloalkenyl) substituents, aromatic-, aliphatic- and alicyclic-substituted aromatic nuclei and the like, as well as cyclic substituents wherein the ring is completed through another portion of the molecule (that is, any two indicated substituents may together form an alicyclic radical).

2. Substituted hydrocarbon substituents, that is, those containing non-hydrocarbon radicals which, in the context of this invention, do not alter the predominantly hydrocarbyl character of the substituent. Those skilled in the art will be aware of suitable radicals (e.g., halo, (especially chloro and fluoro), amino, alkoxyl, mercapto, alkylmercapto, nitro, nitroso, sulfoxy, etc.).

3. Hetero substituents, that is, substituents which, while predominantly hydrocarbon in character within the context of this invention, contain atoms other than carbon present in a chain or ring otherwise composed of carbon atoms.

The compositions of the present invention also include specific compounds which are illustrated by the following the formulas II, III & IV, below:

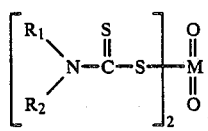  (II)

and

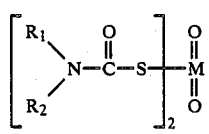  (III)

wherein M, $R_1$ and $R_2$ are the same as previously defined above.

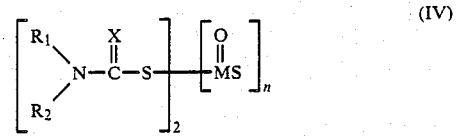  (IV)

wherein M, $R_1$, $R_2$ and X are the same as previously defined above and n is at least 2. A preferred structure defined by the above formula (IV) is:

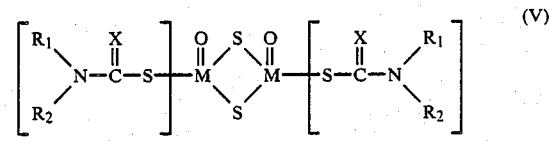  (V)

wherein $R_1$ and $R_2$, M and X are the same as previously defined above. As a most preferred species, $R_1$ is alkyl of about 12 to about 18 carbon atoms, $R_2$ is hydrogen, M is Mo and X is S.

As illustrated by the above formulas, the preferred composition within the scope of the present invention are compositions wherein the metal cation is in the oxidation state of +5 or +6. Furthermore, complexes of these compositions are compounds, preferably the pentavalent species with thiourea type molecules are also intended to be within the scope of the present invention. Additionally, oligomers formed by the reaction of sulfur with unsaturated sites on the hydrocarbyl group, are contemplated within the scope of this invention, e.g., when $R_1$ is oleyl. This reaction may occur with 2 molecules of the metal containing composition or with other species present containing ethylenically unsaturated sites.

The compositions described above are preferably prepared as follows:

1. reacting at least one hydrocarbyl primary amine with a $CS_2$ source or COS source; followed by 2. reacting the product of reaction 1. (above) with a molybdenum or tungsten containing compound.

As discussed in the Background of the Invention, the surprising development of the present invention is the preparation of these compounds from hydrocarbyl primary amines as opposed to secondary amines. The following general reaction scheme is illustrative of the process according to the present invention.

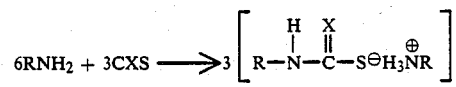

wherein R is independently hydrocarbyl and X is O or S.

2. The product of Reaction 1 + metal-containing compound $\xrightarrow{}$ compound of formulation (I) + by-products.

The reaction is generally conducted in the presence of a substantially inert, normally liquid organic diluent/solvent such as benzene, toluene, xylene, petroleum naphtha, mineral oil, ethyleneglycol monomethylether or the like. The first step, i.e., the reaction of the primary amine with the $CS_2$ source or COS source, is usually conducted in an inert atmosphere (e.g., purged with $N_2$). Since this reaction is exothermic, it is necessary to cool the reaction container to maintain the reaction mixture preferably at a temperature in the range of about 20° C. to about 40° C.

After which, the above reaction product is reacted with the particular metal containing compound to form the final thiocarbamate product.

As indicated above, the amine reactants useful in the preparation of the compositions of the present invention are hydrocarbyl primary monoamines. The amine reactants of the present invention may contain such radicals as aliphatic, cycloaliphatic, and aromatic, including aliphatic-substituted aromatic, and aliphatic-substituted cycloaliphatic radicals. The amine substituent is not particularly critical only to the extent that the amine is a primary amine and is, in turn, capable of forming a thiourea to result in the elimination of $H_2S$ in situ. (Note the reaction scheme set out above.) Illustrative of such primary monoamines are methylamine, ethylamine, n-butylamine, hexylamine, octylamine, dodecylamine, stearylamine and oleylamine. Also, diamines of the formula:

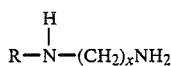

where R is hydrocarbyl and x is 2–4 carbon atoms are useful reactants within the scope of the present invention. It should be understood that while at least one amine reactant must be a primary amine, the reaction mixture may comprise a mixture of primary and secondary amines wherein at least 25 mole percent of the amine mixture is primary amines. Oleylamine or a mixture of stearylamine and oleylamine are the preferred reactants.

The above hydrocarbyl primary amines are initially reacted as described above with carbon disulfide, carbonylsulfide, or a source material that releases either one of these reactants in solution.

The reaction product of the amine with carbon disulfide or carbonylsulfide is then reacted with a metal containing compound. This metal containing compound is either a tungsten or molybdenum compound. While the particular molybdenum or tungsten compound useful to prepare the carbamate compounds according to the present invention is not particularly critical, the oxide compound is the preferred molybdenum compound reactant and the hexavalent oxide of molybdenum is the most preferred ($MoO_3$). However, various heteropolyacidic compounds such as the phospho compound, as well as the halides or oxyhalides have also been found to be useful. Also, the molybdic and tungstic acids ($H_2MoO_4$ and $H_2WO_4$) may be used to prepare the compositions of the invention.

More detailed discussion of the nature of useful molybdenum and tungsten compounds, as well as their chemistry, preparation and physical properties can be found in F. A. Cotton and G. Wilkinson, *Advanced Inorganic Chemistry, A Comprehensive Text*, Second Edition, Interscience Publisher-A Division of John Willey & Sons, New York (1966), Pages 930–960, which is hereby incorporated by reference for the disclosures in this regard. Additionally, a large number of suitable molybdenum compounds are disclosed in Kirk-Othmer, *Encyclopedia of Chemical Technology*, Second Edition, Volume 13, Pages 648–652, which is also incorporated by reference herein for such disclosure.

For the purposes of this invention, it is necessary that the reaction of the amine with the $CS_2$ or COS source be carried out prior to reaction with the metal containing compound. By conducting the reaction according to this two step process and by utilizing a primary amine, the advantage of in situ generation of hydrogen sulfide results which is required to produce the desired product according to the present invention. Moreover, it gives the additional advantage of producing a product of lower stability which is required for the beneficial anti-wear performance and to function as an anti-oxidant. It is pointed out, however, that hydrogen sulfide may also be introduced from an external source in one embodiment of the present invention.

With respect to the relative amounts of the different reactants utilized to prepare the products according to the present invention, no specific amount of any of the reactants is particularly critical to the present invention. For the sake of ease and simplicity, standard stoichiometry for this reaction may be employed. Specifically, carbon disulfide, carbonyl sulfide or source materials for these reactants will be reacted with at least one hydrocarbyl primary amine in at least a 1:2 ratio. The ratio of the carbon disulfide ($CS_2$), carbonyl sulfide (COS) or source materials for these reactants to the primary amine may range from about 0.5:4 to about 1:1. As a most preferred embodiment, the ratio of the carbon disulfide, carbonyl sulfide or source materials for these reactants to the amine reactants is 2.5:4 or 2.5:2 (primary amines):2 (secondary amines).

With respect to the amount of the metal-containing compound, it is pointed out that the amount of metal-containing compound is not particularly critical to the present invention, and the amount used in the reaction may vary over a wide range. As a most preferred embodiment, approximately 1 mole of the metal-containing compound will be reacted with approximately 2 moles of the reaction product of the amine with the carbon disulfide, carbonyl sulfide or source material for these reactants. However, the amount of metal-containing compound to the amine-$CS_2$ or COS reaction product may range from about 1:1 to about 1:4. Other parameters, such as economics and total amount of product desired will generally be the controlling factors for the amount used. As a most preferred embodiment, the ratio of the three reactants, i.e., the amine/$CS_2$, COS/metal containing compound, is about 4:2.5:1.

As indicated above, the first step reaction is exothermic. It is, therefore, necessary to cool the reaction container, e.g., if $CS_2$ is the reactant, it would be necessary to maintain the temperature below its flash point of 46° C. For the purposes of the present invention, it is preferred to maintain the temperature of the reaction container in the range of about 20° C. to about 40° C.

The reaction product of step 1 is then melted at a temperature below about 40° C. to inhibit decomposition and the release of $H_2S$. The melt is then reacted with the metal containing compound at a temperature in the range of about 75° C. to about 115° C. A preferred temperature range is 90° C. to about 100° C. The most preferred temperature is about 95° C. The reaction mixture is held at the particular reaction temperature for about 4 hours to about 24 hours. After which, the volatiles are taken off and removed and the final product purified. As previously pointed out, another embodiment of the present invention contemplates the addition of external $H_2S$ to the reaction mixture which further contains olefin to react with the excess sulfur produced. The addition of external $H_2S$ would depend upon the desired sulfur content of the final product which is controlled by its final end use.

The preparation of specific compositions of the present invention are further illustrated in the examples that follow. While these examples are presented to show one skilled in the art how to operate within the scope of this invention, they are not to serve as a limitation on the scope of the invention where such scope is defined only in the claims. It is pointed out that in the following examples, and elsewhere in the present specification and claims, all percentages, as well as all parts, are intended to express percent by weight and parts by weight unless otherwise specified.

EXAMPLE I

Toluene (1420 g) and oleylamine (4825 g) (obtained as ARMEEN TM OL from Armour & Co.) were charged to a 12-liter four-necked flask. This flask was equipped with a stirrer, thermowell, subsurface addition tube and a condenser. The reaction mixture was purged with $N_2$ (0.1 SCF/Hr) and vented to a caustic trap to collect any $H_2S$ or $CS_2$ which might escape during the reaction.

$CS_2$ (855 g) was added dropwise through the subsurface addition tube over 5 to 6 hours. The reaction was exothermic and cooling of the flask was necessary to keep the reaction mixture between 20°–40° C. (Carbon disulfide boils at 46° C. and has a flash point of −30° C.). After the addition was complete, the mixture was a slightly viscous green-gray solution.

If the reaction mixture at this point in the reaction sequence cools and stands at room temperature (25°) for several hours, it will crystallize to a solid mass. Then, in order to proceed to the next step, the solid mass must be melted by an external heat source of not greater than 40° C. At temperatures higher than 40° C., this intermediate begins to decompose with the release of copious amount of $H_2S$.

After holding the reaction mixture at 40° C. for ¼ hour, the $MoO_3$ (648 g) was added in one portion. The $MoO_3$ was stirred into the reaction mixture to obtain a uniform heterogeneous mixture; this usually took about 15 minutes. It was then heated to 95° C. for over 2 hours.

The mixture was held at 95° C. for 18 hours.

The mixture then was heated to 130° C. and with a $N_2$ purge of 1 SCF/Hr, the volatiles (water and toluene) were removed. 162/162 grams of water were collected.

After holding at 130° C. for ½ hour, the product was vacuum stripped at 130° C. and 5–10 mm Hg to remove the last traces of water and toluene.

The product was filtered at 130° C. through 60 grams of diatomaceous earth filter aid. The filtered product cools to a red-brown, waxy solid.

Yield: 5700 grams (92.4%)
Analysis:

| Analysis: | |
|---|---|
| Mo = 7.22/7.00 | S = 11.35/11.67 |
| N = 4.06/4.10 | TAN = 40.5 |
| TBN = 58.7 | DAN = 29.8 |
| Melting Point (pour point) = +18° C. | |
| Density = 1.0055 | |

EXAMPLE II

Oleyl amine (1756 g, 6.62 m) (obtained as ARMEEN TM OL from Armour & Co.) and toluene (257 g) were stirred in a flask. $CS_2$ (315 g, 4.14 m) was added to the mixture dropwise to control the exotherm such that 41° C. was not exceeded. The total addition time was 5 hrs. A clear, viscous, yellow-green solution was obtained. The mixture was melted at 50° C. (completely fluid) and $MoO_3$ (239 g, 1.66 m) was added and the mixture was further heated to 98° C.–100° C. The mixture refluxed for 5 hrs. at 98° C.–100° C. The mixture was then vacuum stripped at 130° C./5 mm Hg. The material was vacuum filtered over 10 g diatomaceous filter aid on a cloth pad, and warmed by a heat lamp. 2162 g (97.3%) red liquid was obtained.

Analysis:

| Analysis: | |
|---|---|
| Mo = 6.77/7.17 | TBN = 56.1 |
| S = 11.52/11.85–11.92 | TAN = 41.2 |
| N = 56.1 | DAN = 29.8 |

EXAMPLE III

To a 5-liter flask was added oleyl amine (1024 g, 14 m), (obtained as ARMEEN TM OL from Armour & Co.) olefin, $C_{15-18}$ olefin (240 g, 1 m) and toluene (205 g). The mixture was stirred and sparged with $N_2$ at 0.25 SCF/hr. To this mixture, $CS_2$ (2228 g, 3 m) was added. The temperature was maintained below 40° C. The addition took 3.5 hrs. The product slowly solidified.

The above product was slowly warmed to 45° C. The reaction mixture became fluid to which was added $MoO_3$ (288 g, 2 m). The mixture was heated to 70° C. and $H_2S$ added at 7 SCF/m. An exotherm was observed at 81° C. The reaction temperature was maintained at between about 85° C. and 90° C.

The $H_2S$ addition was discontinued after 4 hours. The mixture was then heated to 130° and purged with $N_2$ at 1 SCF/hr. After holding this mixture at 130° for one-half hour, the product was vacuum stripped at 130° C. and 5–10 mm Hg to remove the waste and toluene. The reaction product was then purified by filtering through 100 g of diatomaceous filter aid with heating.

Yield: 980 g, 50% of theoretical
Analysis:

| Analysis: | |
|---|---|
| TAN = 46.7/57 | S = 13.12/13.35–14.14 |
| Mo = 10.8 | |
| N = 3.21/3.27 | Cu Strip: 2c (3 hrs.) |
| TBN = 36.1/32.9 | |

EXAMPLE IV

In this example, the same procedure is followed as described in Example I. Only for this example, $WO_3$ (1044 g) is substituted for the $MoO_3$.

EXAMPLE V

For this example, the procedure of Example II is followed. However, n-butylamine (483 g) is substituted for the oleylamine.

The compositions according to the present invention, which specific species are illustrated in the above examples, are versatile additives for functional fluids including lubricants. The compositions of the present invention have been found to be useful additives for improving anti-wear properties, anti-oxidant properties, extreme pressure properties and friction modifying properties of lubricant compositions. Also, the compositions of the present invention may find use in other functional fluids including fuel compositions, automatic transmission fluids, hydraulic fluids and metal working fluids.

The composition of the present invention may be formulated with a functional fluid by the direct blending of the composition to the particular functional fluid, e.g., lubricant composition, or it may be formulated with the functional fluid in the form of a concentrate. Such a concentrate may be prepared by adding 1% to about 99% by weight of the composition of the present invention to a substantially inert, normally liquid organic diluent or solvent such as benzene, toluene, xylene, petroleum naphtha, mineral oil, ethyleneglycol monomethyl ether or the like.

The compositions of the present invention formulated with the particular functional fluid may contain other additives and chemistries such as dispersants, other anti-oxidants, and the like. Such other additives and chemistries include, for example, detergents and dispersants of the ash-producing or ashless type, corrosion- and oxidation-inhibiting agents, pour point depressing agents, auxiliary extreme pressure agents, color stabilizers and anti-foam agents. These other additives and chemistries are fully described and disclosed in U.S. Pat. No. 3,541,014 to LeSuer; U.S. Pat. No. 4,289,635 to Schroeck; and U.S. Pat. No. 4,266,945 to Karn, which patents were cited in the state of the art section of this specification. The disclosures of these patents relating to such other additives and chemistries are hereby incorporated by reference for such disclosures.

To further illustrate various functional fluid compositions, specifically lubricant compositions, comprising the compositions of the present invention the following illustrative examples are provided. It is again pointed out that the following examples are provided for illustrative purposes only and are not to place any limitation on the scope of the invention where such scope is set out only in the claims. All parts and percentages are by weight.

Table I sets out the results from testing the compound of EXAMPLE I in the standard OLDSMOBILE SEQUENCE IIID TEST.

The procedure followed for this test follows:

This test procedure is designed to evaluate the high temperature performance of engine oils. The principal objective is to produce oil thickening resulting from oxidation. Sequence IIID, replacing Sequence IIIC, also evaluates sludge, varnish and wear characteristics of motor oils.

The test relates to field service where engine design and car usage have produced higher oil temperatures and resultant cases of oil thickening. The problem has been aggravated by trailer towing, power-consuming accessories, emission control devices and extended high speed driving on freeways.

Basic equipment such as the automatic controls and jacketed rocker covers used for the IIID test are likewise employed in the IIID sequence. A 100% glycol coolant is needed because of the high engine operating temperatures. Coolant outlet temperature is maintained at 118° C. (245° F.), and the oil temperature at 149° C. (300° F.).

The test consists of operation at 100 BHP at 3000 rpm with a maximum test length of 64 hours. The test is terminated when the oil level shows more than 28 ounces low at any of the eight-hour oil check intervals. When tests are concluded before 64 hours because of low oil level, the low oil level has generally resulted from hang-up of the heavily oxidized oil throughout the engine and inability to drain down to the oil pan at the 49° C. (120° F.) oil check temperature.

Viscosities are obtained on the eight-hour oil samples and from this data curves are plotted of percent viscosity increase versus engine hours. A 375% viscosity increase measured at 40° C. (104° F.) at 40 hours is allowed, and the 64-hour test must be completed. The engine sludge requirement is a minimum of 9.2 and piston skirt varnish a minimum of 9.1 based on the CRC merit rating system.

TABLE I

| COMPONENTS | LUBRICANT EXAMPLE | |
|---|---|---|
| | A | B |
| Base Oil | 86.568 | 84.61 |
| Product of Example I | — | 2.0 |
| Reaction Product of Maleic Anhydride-Styrene Copolymer with Alcohol and Amine | .12 | .08 |
| Hydrogenated styrene Isoprene Non-dispersant Viscosity Improver | 9.0 | 9.0 |
| 2,5-Bis(tert-octyldithio) thiadiazole | .1 | .1 |
| Alkylated Aryl Amine | .42 | .42 |
| Sulfurized Olefin | 1.275 | 1.275 |
| Polybutenyl Succinic Anhydride-ethylene Polyamine Reaction Product | 1.70 | 1.70 |
| Basic Magnesium Petroleum Sulfonate | .81 | .81 |
| Silicon Antifoamant | .007 | .005 |

Oldsmobile Sequence IIID Test
Lubricant A - The viscosity increase is too viscous to measure (control)
Lubricant B - % viscosity increase is 73

Table II sets out results of testing the compound of EXAMPLE II for extreme pressure properties. The results for the MHL data were obtained according to the procedures according to ASTM D-2783-87 (4-ball) and the standard SAE at 1000 rpm test.

TABLE II

| COMPONENTS | EXAMPLE # (PERCENT BY WEIGHT) | |
|---|---|---|
| | C | D |
| Mineral Oils | 94.20 | 94.20 |
| Reaction Product of Maleic anhydride copolymer with alcohol and amine | 0.40 | 0.40 |
| Polyisobutenyl succinic anhydride-ethylene polyamine reaction product | 0.60 | 0.60 |
| Sulfurized isobutene | 3.5 | 3.5 |
| Silicone antifoam | 0.005 | 0.005 |
| Amine-neutralized phosphate ester of hydroxyalkyl dialkylphosphorodithioate | 1.20 | |
| Product of Example I | | 1.20 |
| Dimercaptothiadizaole based inhibitor | 0.10 | 0.10 |
| MHL | 126 | 100 |
| | 315 | 400 |
| | 55.56 | 58.68 |
| SAE @ 1000 | 437 | 487 |

While the invention has been described and illustrated with reference to certain preferred embodiments thereof, those skilled in the art will appreciate that various changes, modifications and substitutions can be made therein without departing from the spirit of the invention. For example, different ratios other than the preferred ranges set forth hereinabove may be applicable as a consequence of variations in the oil base stock, type of engine or the like. It is intended, therefore, that the invention be limited only by the scope of the claims which follow:

What is claimed is:

1. A composition comprising:

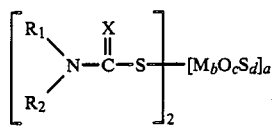

wherein $R_1$ and $R_2$ are independently the same or different and are selected from H and hydrocarbyl with the proviso that at least one of $R_1$ or $R_2$ is H for at least one of the thiocarbamate groups, and at least one of $R_1$ or $R_2$ is hydrocarbyl for each of the thiocarbamate groups, M is Mo or W, X is O or S, b is at least 1, a is at least 1 depending on the oxidation state of M, c is at least 1 depending on the oxidation state of M and d is 0 or at least 1 depending on the oxidation state of M.

2. The composition according to claim 1, wherein M is Mo, X is S, $R_1$ is hydrocarbyl of 1 to about 750 carbon atoms, $R_2$ is hydrogen, a is 1 or 2, b is 1 or 2, c is 2 and d is 0 if a and b are 1 and d is 2 if a and b are 2.

3. The composition according to claim 1, wherein M is Mo, X is S, $R_1$ is oleyl, $R_2$ is hydrogen, a is 1, b is 1, c is 2 and d is 0.

4. The composition according to claim 1, wherein M is Mo, X is S, $R_1$ is oleyl, $R_2$ is hydrogen, a is 2, b is 1, c is 1 and d is 1.

5. The composition according to claim 1, wherein M is Mo, X is O, $R_1$ is oleyl, $R_2$ is hydrogen, a is 2, b is 1, c is 1 and d is 1.

6. The composition according to claim 1 which further comprises a mixture with a thiourea of the formula:

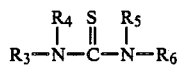

wherein $R_3$ and $R_6$ are independently the same or different and are hydrogen or hydrocarbyl with the proviso that at least one of $R_3$ or $R_6$ is hydrogen and $R_4$ and $R_5$ are independently the same or different and are hydrocarbyl.

7. The composition according to claim 2 which further comprises a mixture with a thiourea of the formula:

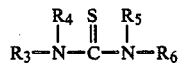

wherein $R_3$ and $R_6$ are independently the same or different and are hydrogen or hydrocarbyl with the proviso that at least one of $R_3$ or $R_6$ is hydrogen and $R_4$ and $R_5$ are independently the same or different and are hydrocarbyl.

8. The composition according to claim 4 which further comprises a mixture with a thiourea of the formula:

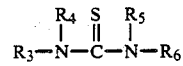

wherein $R_3$ and $R_6$ are independently the same or different and are hydrogen or hydrocarbyl with the proviso that at least one of $R_3$ or $R_6$ is hydrogen and $R_4$ and $R_5$ are independently the same or different and are hydrocarbyl.

9. The composition according to claim 1, wherein said composition comprises oil-soluble oligomers of said composition defined by Formula I.

10. The composition according to claim 9, wherein said oligomer is obtained by the reaction of a sulfur containing reagent with an unsaturated site in said hydrocarbyl group to form a sulfide or polysulfide linkage with the hydrocarbyl group of a second molecule of the metal composition defined by Formula (I) or other ethylenically unsaturated containing molecule present in the mixture.

11. The composition according to claim 2, wherein said composition comprises oil-soluble oligomers of said metal composition defined by Formula (I).

12. The composition according to claims 4, 6 or 8 wherein said composition comprises oil-soluble oligomers of said metal composition defined by Formula (I).

13. A process for preparing the composition according to claim 1, which process comprises:
   (A) reacting at least one primary amine of the formula $R—NH_2$ wherein R is hydrocarbyl with a $CS_2$ or COS source reagent and;
   (B) reacting the product of (A) with a molybdenum or tungsten containing compound.

14. The process according to claim 13, wherein $H_2S$ is introduced into the reaction medium.

15. The process according to claim 13, wherein $H_2S$ is produced in situ by the reaction of said primary amine with said $CS_2$ or COS source reagent.

16. The process according to claim 13, wherein the hydrocarbyl amine compound of step (A) is selected from the group consisting of a Mannich base, alkylamines, aralkylamines, arylamines, a carboxylic acid amide, a carboxylic acid imide or mixtures thereof.

17. The process according to claim 16, wherein the hydrocarbyl group of the primary amine of step (A) contains up to about 750 carbon atoms.

18. The process according to claim 16, wherein said amine is an aromatic amine, an aliphatic amine or mixtures thereof.

19. The process according to claim 13, wherein step (A) is conducted in the presence of an aromatic hydrocarbon solubilizing agent, an alcohol solvent or an aliphatic hydrocarbon solvent.

20. The process according to claim 13, wherein said molybdenum compound is a hexavalent molybdenum compound.

21. The process according to claim 13 wherein the reaction product of (A) and (B) yields a pentavalent molybdenum and nitrogen-containing hydrocarbyl composition.

22. The process according to claim 13, wherein the reaction product of (A) and (B) is a complex of a hydrocarbyl substituted thiourea with a pentavalent molybdenum and nitrogen-containing hydrocarbyl composition.

23. The process according to claims 21 or 22, wherein the hydrocarbyl substituent is oleyl, and $CS_2$ is the reagent used to react with said hydrocarbyl amine in Step (A).

24. A compound of the formula:

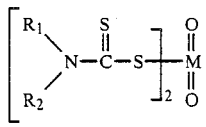 (II)

wherein $R_1$ and $R_2$ are independently the same or different and are selected from H and hydrocarbyl with the proviso that at least one of $R_1$ and $R_2$ is H for at least one of the thiocarbamate groups, and at least one of $R_1$ and $R_2$ is hydrocarbyl for each of the thiocarbamate groups, and M is Mo or W.

25. The compound of claim 24, wherein $R_1$ is hydrocarbyl containing an alkyl group of 1 to about 750 carbon atoms or aralkyl of about 8 to about 750 carbon atoms.

26. The compound of claim 25, wherein $R_1$ is oleyl.

27. A compound of the formula:

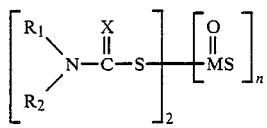 (IV)

wherein $R_1$ and $R_2$ are independently the same or different and are selected from H and hydrocarbyl with the proviso that at least one of $R_1$ or $R_2$ is H for at least one of the thiocarbamate groups, and at least one of $R_1$ or $R_2$ is hydrocarbyl for each of the thiocarbamate groups, n is at least 2, X is O or S and M is Mo or W.

28. The compound of claim 27 wherein R is hydrocarbyl containing an alkyl group of about 1 to about 750 carbon atoms or aralkyl of about 8 to about 750 carbon atoms.

29. The compound of claim 28, wherein R is oleyl.

30. The compound of claim 27 of the formula:

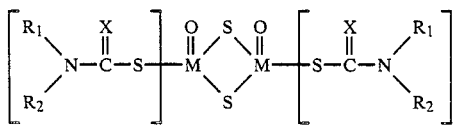 (V)

wherein $R_1$ and $R_2$, M and X are the same as defined in claim 27.

31. A complex comprising
(A) a thiourea of the formula:

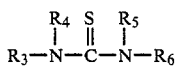 (VI)

and

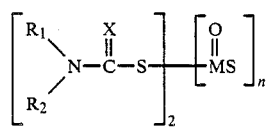 (IV)

wherein $R_3$ and $R_6$ are independently the same or different and are hydrogen or hydrocarbyl with the proviso that at least one of $R_3$ or $R_6$ is hydrogen and are independently the same or different and $R_4$ and $R_5$ are hydrocarbyl, $R_1$ and $R_2$ are independently the same or different and are selected from H and hydrocarbyl with the proviso that at least one of $R_1$ or $R_2$ is H for at least one of the thiocarbamate groups, and at least one of $R_1$ or $R_2$ is hydrocarbyl for each of the thiocarbamate groups, n is at least 2, x is O or S and M is Mo or W.

32. The complex of claim 31, wherein $R_1$ is hydrocarbyl containing an alkyl group of about 1 to about 750 carbon atoms or aralkyl of about 8 to about 750 carbon atoms.

33. The complex of claim 31, wherein $R_1$ is oleyl.

34. The complex according to claim 32, which further comprises sulfurized olefin.

35. An additive for improving the antiwear properties, antioxidant properties, extreme pressure properties and friction modifying properties of lubricant compositions comprising the composition of claim 1.

36. An additive for improving the antiwear properties, antioxidant properties, extreme pressure properties and friction modifying properties of lubricant compositions comprising the composition of claim 4.

37. An additive for improving the antiwear properties, antioxidant properties, extreme pressure properties and friction modifying properties of lubricant compositions comprising the composition of claim 27.

38. An additive for improving the antiwear properties, antioxidant properties, extreme pressure properties and friction modifying properties of lubricant compositions comprising the composition of claim 6.

39. An additive for improving the antiwear properties, antioxidant properties, extreme pressure properties and friction modifying properties of lubricant compositions comprising the composition of claim 31.

40. An additive for improving the antiwear properties, antioxidant properties, extreme pressure properties and friction modifying properties of lubricant compositions comprising the composition of claim 9.

41. A concentrate comprising a diluent or solvent and 1% to about 99% by weight of the additive of claim 35.

42. A concentrate comprising a diluent or solvent and 1% to about 99% by weight of the additive of claim 37.

43. A concentrate comprising a diluent or solvent and 1% to about 99% by weight of the additive of claim 39.

44. A lubricant composition comprising a major amount of a lubricating oil and a minor amount of the composition of claim 1.

45. A lubricant composition comprising a major amount of a lubricating oil and a minor amount of the composition of claim 4.

46. A lubricant composition comprising a major amount of a lubricating oil and a minor amount of the composition of claim 27.

47. A lubricant composition comprising a major amount of a lubricating oil and a minor amount of the composition of claim 6.

48. A lubricant composition comprising a major amount of a lubricating oil and a minor amount of the composition of claim 31.

49. A lubricant composition comprising a major amount of a lubricating oil and a minor amount of the composition of claim 9.

50. A fuel composition comprising a major amount of a fuel and a minor amount of the composition of claims 24, 27 or 31.

51. A composition useful as an additive for functional fluids derived from:

(A) at least one hydrocarbyl primary amine reacted with a CS$_2$ or COS source reagent, and
(B) the product of (A) reacted with a molybdenum or tungsten-containing compound.

52. The composition according to claim 51, wherein the primary amine is an oleyl amine which is reacted with CS$_2$ and this reaction product is further reacted with molybdenum trioxide.

53. The composition according to claim 52, wherein H$_2$S is introduced to the reaction mixture.

54. The composition according to claim 53, wherein said reaction is further conducted in the presence of an olefin.

55. A lubricant composition comprising a major amount of a lubricating oil and a minor amount of the composition of claim 51 or 52.

56. A fuel composition comprising a major amount of a fuel and a minor amount of the composition of claim 51 or 52.

* * * * *